US011833053B2

(12) United States Patent
Reeder et al.

(10) Patent No.: US 11,833,053 B2
(45) Date of Patent: *Dec. 5, 2023

(54) ORTHOPAEDIC PROSTHETIC SYSTEM FOR A HINGED-KNEE PROSTHESIS

(71) Applicant: DePuy Ireland Unlimited Company, Ringaskiddy (IE)

(72) Inventors: Nathan C. Reeder, Warsaw, IN (US); Tyler S. Hathaway, Auburn, IN (US)

(73) Assignee: DePuy Ireland Unlimited Company, Ringaskiddy (IE)

(*) Notice: Subject to any disclaimer, the term of this patent is extended or adjusted under 35 U.S.C. 154(b) by 615 days.

This patent is subject to a terminal disclaimer.

(21) Appl. No.: 16/990,168

(22) Filed: Aug. 11, 2020

(65) Prior Publication Data

US 2020/0368030 A1    Nov. 26, 2020

Related U.S. Application Data

(63) Continuation of application No. 15/969,737, filed on May 2, 2018, now Pat. No. 10,736,748.

(51) Int. Cl.
*A61F 2/38*    (2006.01)
*A61F 2/30*    (2006.01)
(52) U.S. Cl.
CPC ............ *A61F 2/3859* (2013.01); *A61F 2/385* (2013.01); *A61F 2/3868* (2013.01); *A61F 2002/30471* (2013.01); *A61F 2002/30604* (2013.01); *A61F 2002/30624* (2013.01); *A61F 2002/30634* (2013.01); *A61F 2002/3863* (2013.01)

(58) Field of Classification Search
CPC .......... A61F 2/38; A61F 2/3836; A61F 2/384; A61F 2/3845; A61F 2/385; A61F 2/3859; A61F 2/389; A61F 2/3868
See application file for complete search history.

(56) References Cited

U.S. PATENT DOCUMENTS

| | | |
|---|---|---|
| 3,852,830 A | 12/1974 | Marmor |
| 3,869,729 A | 3/1975 | Attenborough |
| 3,953,899 A | 5/1976 | Charnley |
| 3,958,278 A | 5/1976 | Lee et al. |
| 4,034,418 A | 7/1977 | Jackson et al. |
| 4,215,439 A | 8/1980 | Gold et al. |
| 4,219,893 A | 9/1980 | Noiles |

(Continued)

FOREIGN PATENT DOCUMENTS

| | | |
|---|---|---|
| DE | 2901009 A1 | 7/1980 |
| DE | 3343606 A1 | 7/1985 |

(Continued)

OTHER PUBLICATIONS

Partial European Search Report, European Application No. 19171270.2, dated Oct. 9, 2019, 13 pages.

(Continued)

*Primary Examiner* — Marcia L Watkins
(74) *Attorney, Agent, or Firm* — BARNES & THORNBURG LLP

(57) ABSTRACT

An orthopaedic prosthetic includes a femoral component including a pair of condyles spaced apart to define an intercondylar notch. A tibial component includes a tray and a platform pivotally coupled to the tray. A modular insert is configured to be selectively coupled to the femoral component to couple the femoral component to the tibial component.

8 Claims, 12 Drawing Sheets

(56) References Cited

U.S. PATENT DOCUMENTS

| | | |
|---|---|---|
| 4,224,697 A | 9/1980 | Murray et al. |
| 4,340,978 A | 7/1982 | Buechel et al. |
| 4,790,853 A | 12/1988 | Engelbrecht et al. |
| 4,838,891 A | 6/1989 | Branemark et al. |
| 4,888,021 A | 12/1989 | Forte et al. |
| 5,314,481 A | 5/1994 | Bianco |
| 5,370,701 A | 12/1994 | Finn |
| 5,413,607 A | 5/1995 | Engelbrecht et al. |
| 5,766,257 A | 6/1998 | Goodman et al. |
| 5,824,096 A | 10/1998 | Pappas et al. |
| 5,824,102 A | 10/1998 | Buscayret |
| 5,871,541 A | 2/1999 | Gerber |
| 5,951,603 A | 9/1999 | O'Neil et al. |
| 5,954,770 A | 9/1999 | Schmotzer et al. |
| 6,019,794 A | 2/2000 | Walker |
| 6,074,424 A | 6/2000 | Perrone et al. |
| 6,117,175 A | 9/2000 | Bosredon |
| 6,264,696 B1 | 7/2001 | Reigner et al. |
| 6,319,283 B1 | 11/2001 | Insall et al. |
| 6,482,209 B1 | 11/2002 | Engh et al. |
| 6,485,519 B2 | 11/2002 | Meyers et al. |
| 6,488,711 B1 | 12/2002 | Grafinger |
| 6,652,587 B2 | 11/2003 | Felt et al. |
| 6,660,039 B1 | 12/2003 | Evans et al. |
| 6,709,461 B2 | 3/2004 | O'Neil et al. |
| 6,723,102 B2 | 4/2004 | Johnson et al. |
| 6,743,258 B1 | 6/2004 | Keller |
| 6,755,864 B1 | 6/2004 | Brack et al. |
| 6,764,516 B2 | 7/2004 | Pappas |
| 6,770,097 B2 | 8/2004 | Leclercq |
| 6,773,461 B2 | 8/2004 | Meyers et al. |
| 6,827,739 B2 | 12/2004 | Griner et al. |
| 6,972,039 B2 | 12/2005 | Metzger et al. |
| 6,984,249 B2 | 1/2006 | Keller |
| 7,115,131 B2 | 10/2006 | Engh et al. |
| 7,232,465 B2 | 6/2007 | Keller |
| 7,303,586 B2 | 12/2007 | Keller |
| 7,326,252 B2 | 2/2008 | Otto et al. |
| 7,572,292 B2 | 8/2009 | Crabtree et al. |
| 7,591,855 B2 | 9/2009 | Keller |
| 7,615,081 B2 | 11/2009 | Justin et al. |
| 7,658,767 B2 | 2/2010 | Wyss |
| 7,918,893 B2 | 4/2011 | Romeis et al. |
| 8,568,485 B2 | 10/2013 | Ries et al. |
| 9,452,054 B2 | 9/2016 | Vicatos |
| 10,736,748 B2 | 8/2020 | Reeder et al. |
| 2001/0003803 A1 | 6/2001 | Leclercq |
| 2001/0018615 A1 | 8/2001 | Biegun et al. |
| 2001/0021877 A1 | 9/2001 | Biegun et al. |
| 2001/0034554 A1 | 10/2001 | Pappas |
| 2001/0034555 A1 | 10/2001 | Pappas |
| 2002/0058997 A1 | 5/2002 | O'Connor et al. |
| 2002/0103541 A1 | 8/2002 | Meyers et al. |
| 2002/0120340 A1 | 8/2002 | Metzger et al. |
| 2002/0138150 A1 | 9/2002 | Leclercq |
| 2002/0156535 A1 | 10/2002 | Pappas |
| 2002/0183850 A1 | 12/2002 | Felt et al. |
| 2003/0009228 A1 | 1/2003 | Meyers et al. |
| 2003/0009229 A1 | 1/2003 | Pappas |
| 2003/0009230 A1 | 1/2003 | Gundlapalli et al. |
| 2003/0009231 A1 | 1/2003 | Gundlapalli et al. |
| 2003/0171815 A1 | 9/2003 | Kana et al. |
| 2003/0208276 A1 | 11/2003 | Berelsman et al. |
| 2004/0006393 A1 | 1/2004 | Burkinshaw |
| 2004/0039450 A1 | 2/2004 | Griner et al. |
| 2004/0054416 A1 | 3/2004 | Wyss et al. |
| 2004/0083003 A1 | 4/2004 | Wasielewski |
| 2004/0102851 A1 | 5/2004 | Saladino |
| 2004/0102852 A1 | 5/2004 | Johnson et al. |
| 2004/0162620 A1 | 8/2004 | Wyss |
| 2004/0186584 A1 | 9/2004 | Keller |
| 2004/0215345 A1 | 10/2004 | Perrone, Jr. et al. |
| 2004/0220676 A1 | 11/2004 | Keller |
| 2004/0225368 A1 | 11/2004 | Plumet et al. |
| 2005/0027365 A1 | 2/2005 | Burstein et al. |
| 2005/0107883 A1 | 5/2005 | Goodfried et al. |
| 2005/0107886 A1 | 5/2005 | Crabtree et al. |
| 2005/0246028 A1 | 11/2005 | Pappas et al. |
| 2006/0265078 A1 | 11/2006 | McMinn |
| 2007/0078517 A1 | 4/2007 | Engh et al. |
| 2008/0021566 A1 | 1/2008 | Peters et al. |
| 2008/0058945 A1 | 3/2008 | Hajaj et al. |
| 2009/0005875 A1 | 1/2009 | Koenemann |
| 2009/0299482 A1 | 12/2009 | Metzger et al. |
| 2009/0319048 A1 | 12/2009 | Shah et al. |
| 2010/0174378 A1 | 7/2010 | Metzger et al. |
| 2011/0040387 A1 | 2/2011 | Ries et al. |
| 2014/0277535 A1 | 9/2014 | Metzger et al. |
| 2015/0018960 A1 | 1/2015 | El Zoghbi et al. |
| 2017/0027706 A1 | 2/2017 | Hagen et al. |
| 2019/0091030 A1 | 3/2019 | Incavo |

FOREIGN PATENT DOCUMENTS

| | | |
|---|---|---|
| DE | 19823325 C1 | 3/2000 |
| EP | 716839 A1 | 6/1996 |
| EP | 724868 A1 | 8/1996 |
| EP | 1099430 A1 | 5/2001 |
| EP | 1721584 A1 | 11/2006 |
| EP | 1872747 A1 | 1/2008 |
| EP | 2042133 A1 | 4/2009 |
| FR | 2589720 A1 | 5/1987 |
| FR | 2601873 A1 | 1/1988 |
| FR | 2612767 A1 | 9/1988 |
| FR | 2760352 A1 | 9/1998 |
| FR | 2776919 A1 | 10/1999 |
| RU | 2114580 C1 | 7/1998 |
| RU | 2145821 C1 | 2/2000 |
| WO | 8702883 A1 | 5/1987 |
| WO | 0113825 A1 | 3/2001 |
| WO | 0217821 A2 | 3/2002 |
| WO | 2020141383 A1 | 7/2020 |

OTHER PUBLICATIONS

"Richards Modular Knee System", Richards Orthopedic catalog, 15 pgs, 1979.

"The femoropatellar endoprosthesis-still of value today?", Fink et al., Z Orthop Ihre Grenzgeb., May/Jun. 1999, 137(3):247-52.

"Bicondylar St. George Sledge Knee Arthroplasty", Stockley et al., Clinical Orthopaedics and Related Research, No. 255, Jun. 1990, pp. 228-233.

"Patellofemoral Arthroplasty: A Three-to-Nine-Year Follow-up Study", Arciero et al., Clinical Orthopaedics and Related Research, No. 236, Nov. 1988, pp. 60-71.

Frederick F. Buechel, MD and Michal J. Pappas, PhD, "New Jersey Low Contact Stress Knee Replacement System. Ten-Year Evaluation of Meniscal Bearings." The Orthopedic Clinics of North America, Apr. 1989, vol. 20(2), pp. 147-177.

R.B. Bourne, MD et al., "Kinematic I and Oxford Knee Arthroplasty. A 5-8-year Follow-up Study", The Journal of Arthroplasty vol. 4, Dec. 1987, pp. 285-291.

H. Shoji et al., "Failed Polycentric Total Knee Prosthesis", The Journal of Bone and Joint Surgery, vol. 58(6); Sep. 1976, pp. 773-777.

FDA Document, KA-012255, Richards Mod II Knee, 56 pages, 1976.

Russian Search Report for Application No. 2019112077/14(023498), dated Dec. 13, 2022, 11 pages.

ORTHOPAEDIC PROSTHETIC SYSTEM FOR A HINGED-KNEE PROSTHESIS

This application is a continuation application and claims priority to U.S. patent application Ser. No. 15/969,737, now U.S. Pat. No. 10,736,748, which was filed on May 2, 2018, the entirety of which is expressly incorporated herein by reference.

TECHNICAL FIELD

The present disclosure relates generally to an orthopaedic prosthesis system, including prosthetic components and methods for assembling the prosthetic components during an orthopaedic joint replacement procedure, and, more particularly, to orthopaedic prosthetic components and methods for assembling the prosthetic components during a knee replacement procedure.

BACKGROUND

Movement (e.g., flexion and extension) of the natural human knee involves movement of the femur and the tibia. Specifically, during flexion and extension, the distal end of the femur and the proximal end of the tibia articulate relative to one another through a series of complex movements. Damage (e.g., trauma) or disease can deteriorate the bones, articular cartilage, and ligaments of the knee, which can ultimately affect the ability of the natural knee to function in such a manner. As a result, knee prostheses have been developed and implanted into surgically-prepared ends of the femur and tibia.

A typical knee prosthesis for a total knee replacement, for example, includes a tibial component or tibial tray coupled to the patient's tibia, a femoral component coupled to the patient's femur, and a tibial insert component positioned between the tibial tray and the femoral component and including a surface to accommodate the condyles of the femoral component. A constrained knee prosthesis, however, may be used when a patient's collateral ligaments have been damaged or are otherwise not able to provide adequate support and stability to the knee. One such constrained knee prosthesis is a hinged knee prosthesis, which typically includes a hinge mechanism to couple the femoral component to one or both of the bearing component and the tibial components in order to constrain and mechanically link the components of the knee prosthesis together. Existing hinge knee designs require either a dedicated hinge knee femoral component, or require the hinge axle to be inserted into the femur, which can be difficult if there is not adequate exposure to hinge axle.

SUMMARY

According to an aspect of the disclosed embodiments, an orthopaedic prosthetic assembly includes a femoral component configured to be coupled to a surgically-prepared distal end of a patient's femur. The femoral component includes a pair of condyles spaced apart to define an intercondylar notch. Each condyle includes a convex curved condylar surface. A tibial component includes a tray configured to be coupled to a surgically-prepared proximal end of a patient's tibia and a platform pivotally coupled to the tray. The platform includes a pair of concave curved surfaces corresponding to the convex curved condylar surfaces of the femoral component and a proximal opening positioned between the concave curved surfaces. A modular insert is configured to be selectively coupled to the femoral component. The modular insert includes a bracket sized to be positioned in the intercondylar notch of the femoral component. An elongated stem is sized to be received in the opening defined in the platform of the tibial component. A hinge pin pivotally couples the elongated stem to the bracket. A fastener is configured to secure the femoral component to the bracket of the modular insert. The platform is configured to pivot about a first axis extending in an inferior-superior direction and the elongated stem is configured to pivot about a second axis relative to the bracket and the femoral component. The second axis extends in a medial-lateral direction orthogonal to the first axis.

In some embodiments, the fastener may extend transverse to the hinge pin. The fastener may extend along an axis that is angled relative to an inferior/superior axis of the elongated stem. The fastener may be configured to extend through a bore formed through the bracket of the modular insert. The fastener may be configured to extend through a post of the femoral component. The bracket may include an inferior surface and a superior surface. The bore formed through the bracket may extend from an opening in the inferior surface to an opening in the superior surface.

In some embodiments, the hinge pin may be sized to be positioned in the intercondylar notch of the femoral component.

In some embodiments, a flange may extend from the bracket of the modular insert and may be configured to engage a surface of the femoral component. The flange may extend from a posterior end of the bracket. The flange may be received in a groove formed in an anterior surface of a posterior cam of the femoral component.

According to another aspect of the disclosed embodiments, an orthopaedic prosthetic assembly includes a femoral component configured to be coupled to a surgically-prepared distal end of a patient's femur. The femoral component includes a pair of condyles spaced apart to define an intercondylar notch. Each condyle includes a convex curved condylar surface. The femoral component also includes a base surface and a pair of planar inner side walls extending from the base surface. The base surface and the inner side walls partially define the intercondylar notch. A tibial component includes a tray configured to be coupled to a surgically-prepared proximal end of a patient's tibia and a platform pivotally coupled to the tray. The platform includes a pair of concave curved surfaces corresponding to the convex curved condylar surfaces of the femoral component and a proximal opening positioned between the concave curved surfaces. A modular insert is configured to be selectively coupled to the femoral component. The modular insert includes a bracket sized to be positioned in the intercondylar notch of the femoral component. An elongated stem is sized to be received in the opening defined in the platform of the tibial component. A hinge pin pivotally couples the elongated stem to the bracket. The hinge pin has a length that is less than a distance between the inner side walls of the femoral component. The modular insert also includes a fastener configured to secure the femoral component to the bracket of the hinge insert. The platform is configured to pivot about a first axis extending in an inferior-superior direction and the elongated stem is configured to pivot about a second axis relative to the bracket and the femoral component. The second axis extends in a medial-lateral direction orthogonal to the first axis.

In some embodiments, the hinge pin may be sized to be positioned between the inner side walls of the femoral component. The bracket may include a pair of outer side walls that are spaced a distance less than a distance between the inner side walls of the femoral component. The inner side walls of the femoral component may include a medial side wall and a lateral side wall. The outer side walls of the bracket may include a medial side wall and a lateral side wall.

In some embodiments, the fastener may extend transverse to the hinge pin. The fastener may extend along an axis that is angled relative to an inferior/superior axis of the elongated stem.

In some embodiments, a flange may extend from the bracket of the modular insert and may be configured to engage a surface of the femoral component. The flange may extend from a posterior end of the bracket. The flange may be received in a groove formed in an anterior surface of a posterior cam of the femoral component.

According to yet another aspect of the disclosed embodiments, an orthopaedic femoral component includes a pair of condyles spaced apart to define an intercondylar notch. Each condyle includes a convex curved condylar surface. A base surface and a pair of planar inner side walls extend from the base surface. The base surface and the inner side walls define a cavity that partially defines the intercondylar notch. A posterior cam is positioned in the intercondylar notch. A groove is formed in an anterior surface of the posterior cam. The cavity is sized to receive a bracket of a modular insert. The groove is configured to receive a flange of the modular insert.

In some embodiments, a post may be provided and an aperture may extend through the post. The aperture may be sized to receive a fastener to secure the femoral component to the modular insert. An opening may be formed in the anterior surface of the posterior cam. The groove may extend from the opening.

BRIEF DESCRIPTION OF THE DRAWINGS

The detailed description particularly refers to the following figures, in which.

DETAILED DESCRIPTION

Figure 1:
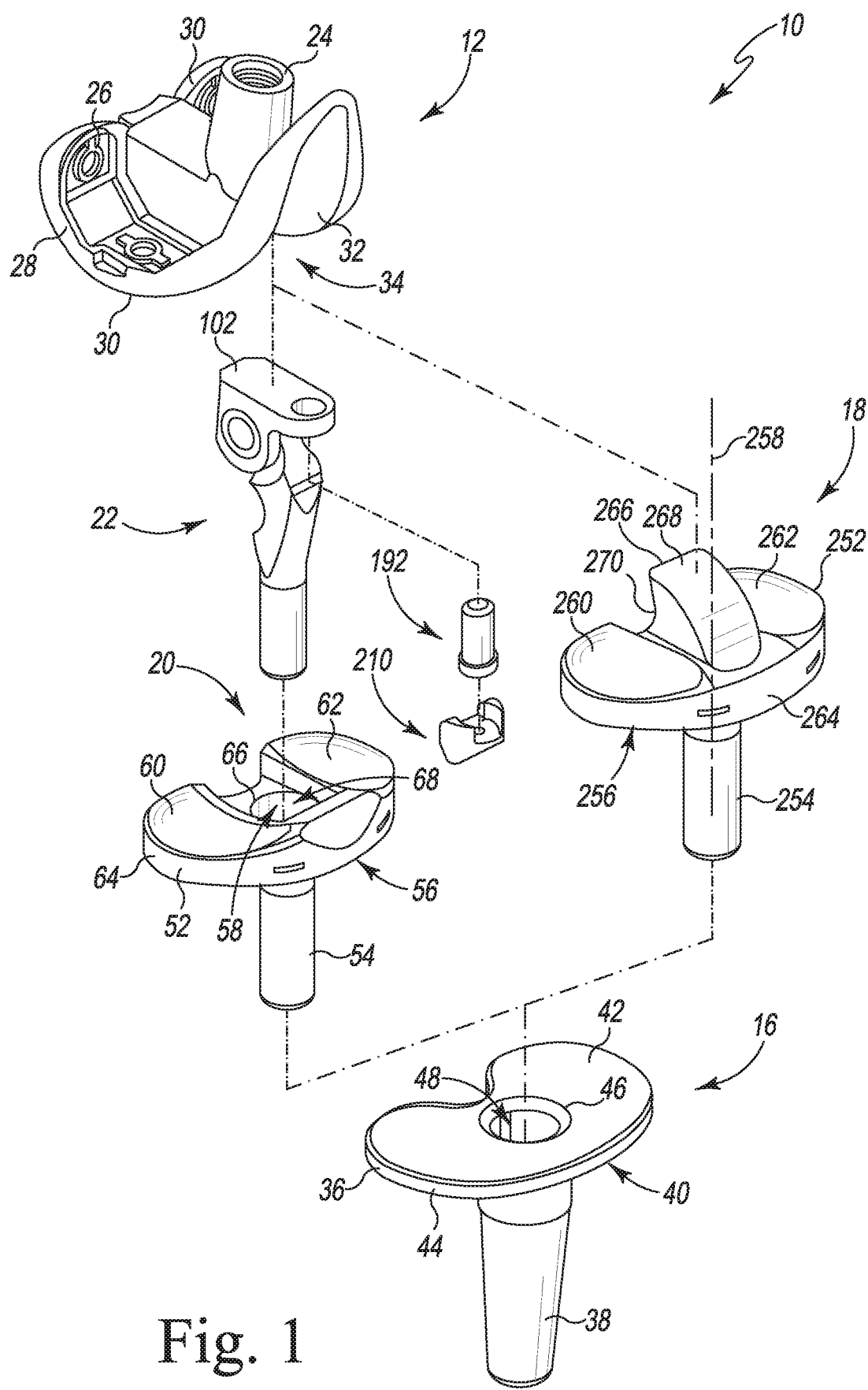
FIG. 1 is an exploded perspective view of an orthopaedic knee prosthesis system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an orthopaedic knee prosthesis system 10 is shown. The orthopaedic knee prosthesis system 10 includes a femoral component 12 configured to be coupled to a distal end of a patient's femur, a tibial tray 16 that is configured to be coupled to a proximal end of a patient's femur, and a pair of tibial inserts 18, 20 configured to be assembled separately with the tibial tray 16. As described in greater detail below, the femoral component 12, the tibial tray 16, and the tibial insert 18 may be assembled to form one type of orthopaedic knee prosthesis; specifically, a rotating platform orthopaedic knee prosthesis. The femoral component 12, the tibial tray 16, the tibial insert 20, and a modular insert 22 may be separately assembled to form another type of orthopaedic knee prosthesis; specifically, a hinged orthopaedic knee prosthesis, as described below.

In the illustrative embodiment, the femoral component 12 includes a post 24 that is configured to be implanted into the distal end of the patient's femur. The post 24 is attached to a body 26 having a pair of spaced-apart lateral and medial condyles 28. The condyles 28 include respective lateral and medial condyle surfaces 30, 32, which are curved convexly. An intercondylar notch 34 is defined between the lateral and medial condyles 28 and is sized to receive the modular insert 22.

The femoral component 12 and the tibial tray 16 are each formed from an implant grade metallic material such as, for example, cobalt chromium. As shown in FIG. 1, the tibial tray 16 includes a base 36 and an anchor 38 that extends inferiorly from a distal surface 40 of the base 36. The base 36 is sized and shaped to conform to the configuration of a surgically-prepared proximal surface of the patient's tibia, and the anchor 38 is sized and shaped to be implanted into a surgically-prepared intramedullary canal of the patient's tibia.

The base 36 includes a substantially planar proximal surface 42 that is positioned opposite the distal surface 40. A curved outer wall 44 extends between from the surfaces 40, 42 and is sized and shaped to conform to the outer edge of the surgically-prepared proximal surface of the patient's tibia. An opening 46 is defined in the proximal surface 42, and the tray 16 includes an aperture 48 that extends inwardly from the opening 46. The aperture 48 extends through the base 36 and into the anchor 38.

The tibial tray 16 may be assembled with one of the tibial inserts 18, 20 shown in FIG. 1 to form a tibial component. Each of the inserts 18, 20 is formed from an implant grade plastic material such as, for example, ultra-high molecular weight polyethylene (UHMWPE). The tibial insert 20 includes a platform 52 that is sized to be positioned on the proximal surface 42 of the tibial tray 16 and an elongated stem 54 that extends inferiorly from a distal surface 56 of the platform 52 along a longitudinal axis 58. Similar to the proximal surface 42 of the tibial tray 16, the distal surface 56 of the platform is substantially planar. The platform 52 also includes a pair of concave curved proximal surfaces 60, 62 that correspond to the lateral and medial condyle surfaces 30, 32 of the femoral component 12. The platform also includes a curved outer wall 64 extends between from the surfaces 56, 60, 62.

As shown in FIG. 1, an opening 66 is defined in the proximal surfaces 60, 62 of the platform 52. The tibial insert 20 also includes an aperture 68 that extends inwardly from the opening 66 through the platform 52 and into the elongated stem 54. The aperture 68 then extends along the longitudinal axis 58 of the stem 54 to a closed end (not shown).

Figure 2:
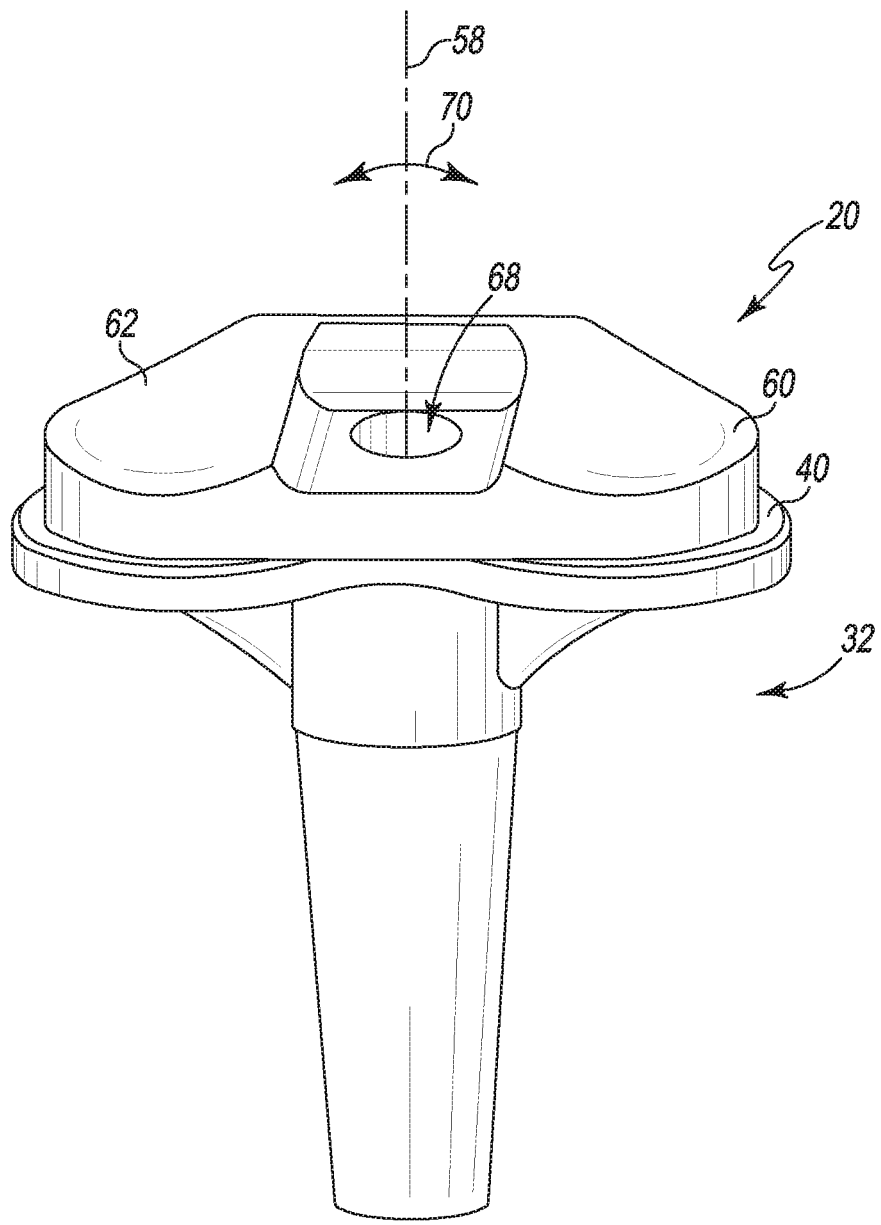
FIG. 2 is a rear perspective view of a tibial component of the orthopaedic knee prosthesis system of FIG. 1.

When coupled to the tibial tray 16 as shown in FIG. 2, the distal surface 56 of the tibial insert 20 engages the proximal surface 42 of the tibial tray. The elongated stem 54 of the tibial insert 20 is sized to be received in the aperture 48 of the tibial tray 16 when the tibial insert is coupled to the tibial tray. In the illustrative embodiment, the stem 54 is sized and shaped to permit the tibial insert 20 to rotate about the longitudinal axis 58 when positioned in the aperture 48 of the tibial tray, as indicated by the arrows 70 in FIG. 2.

Figure 3:
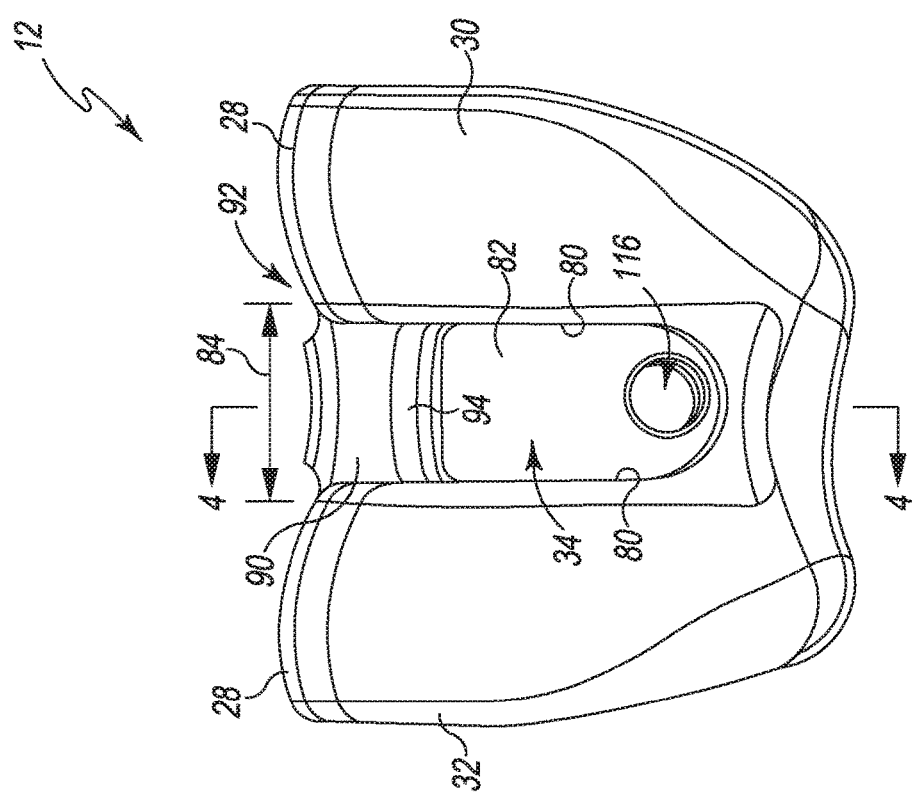
FIG. 3 is a distal plan view of the femoral component of the orthopaedic knee prosthesis system of FIG. 1.

As described above, the tibial tray 16 and the tibial insert 20 may be combined with the femoral component 12 and the modular insert 22 to form a hinged orthopaedic knee prosthesis. Referring now to FIG. 3, the femoral component 12 includes an intercondylar notch 34 that is defined between the medial and lateral condyles 28. Each condyle 28 includes a sidewall 80 that extends distally from a respective condyle surface 30, 32 to a base wall 82. The intercondylar notch 34 has a width 84 that is defined between the sidewalls 80, which is sized to receive the proximal end of the modular insert 22, as described in greater detail below.

Figure 4:
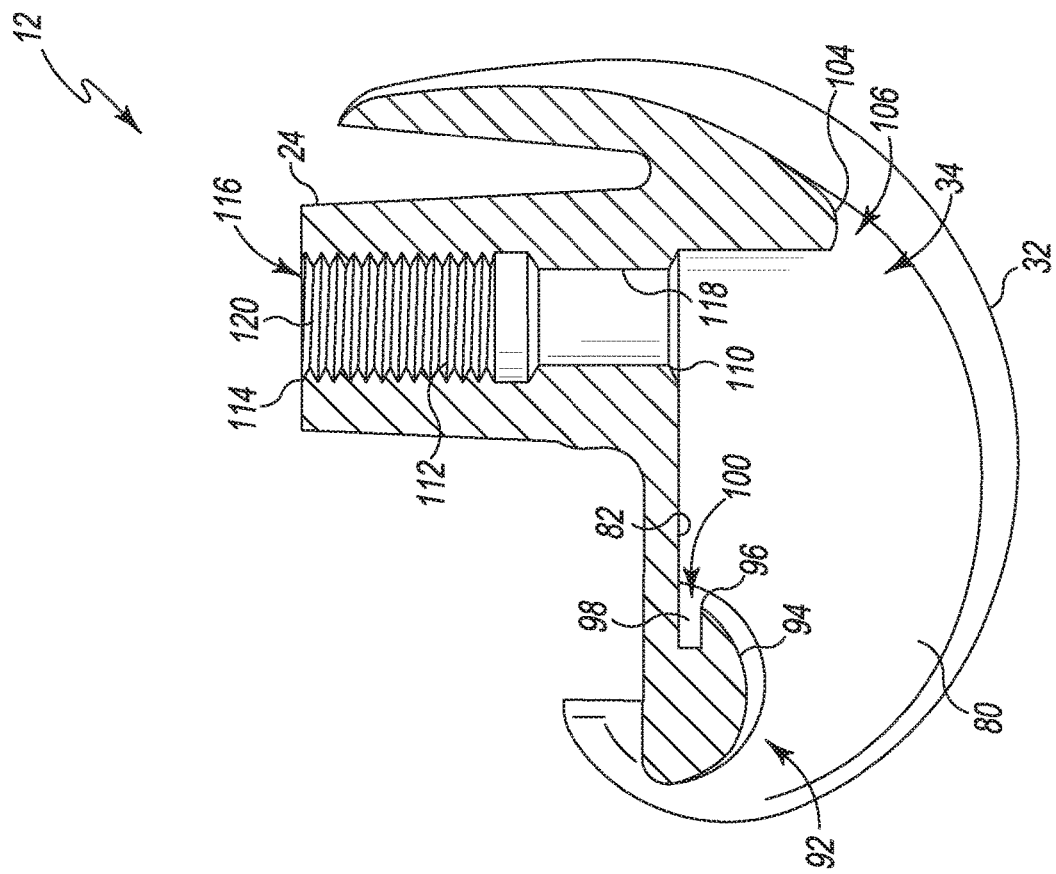
FIG. 4 is a cross-sectional side elevation view of the femoral component taken along the line 4-4 in FIG. 3.

In the illustrative embodiment, the femoral component 12 also includes a posterior cam 90 that extends between the sidewalls 80 at a posterior end 92 of the intercondylar notch 34. As shown in FIGS. 3-4, the posterior cam 90 has a curved anterior surface 94. An opening 96 is defined in the anterior surface 94 adjacent to the base wall 82. A number of walls 98 extend inwardly from the opening 96 to define a groove 100 in the anterior surface 94. As described in greater detail below, the groove 100 is sized to receive a retaining flange 102 of the modular insert 22 to couple the modular insert 22 to the femoral component 12.

As shown in FIG. 4, the femoral component 12 includes an anterior flange 104 that extends between the sidewalls 80 at an anterior end 106 of the intercondylar notch 34. An opening 110 is defined in the base wall 82 adjacent to the anterior flange 104. An inner wall 112 extends proximally from the opening 110 through the post 24 to an opening 114 defined in the proximal end of the post. The inner wall 112 and the openings 110, 114 define a passageway 116 extending through the post 24. The inner wall 112 includes a substantially smooth distal section 118 that is connected to a threaded proximal section 120.

Figure 6:
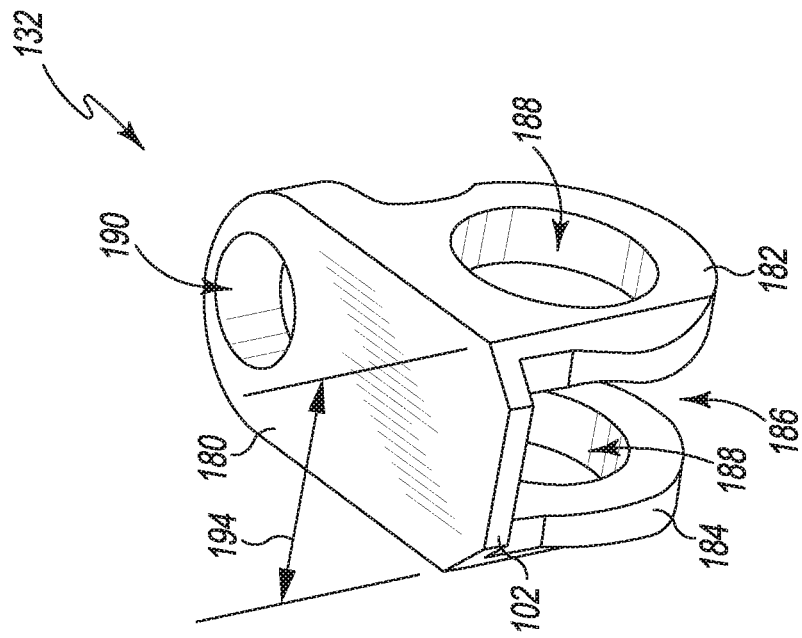
FIG. 6 is a perspective view of a bracket of the modular insert of FIG. 5.
Figure 5:
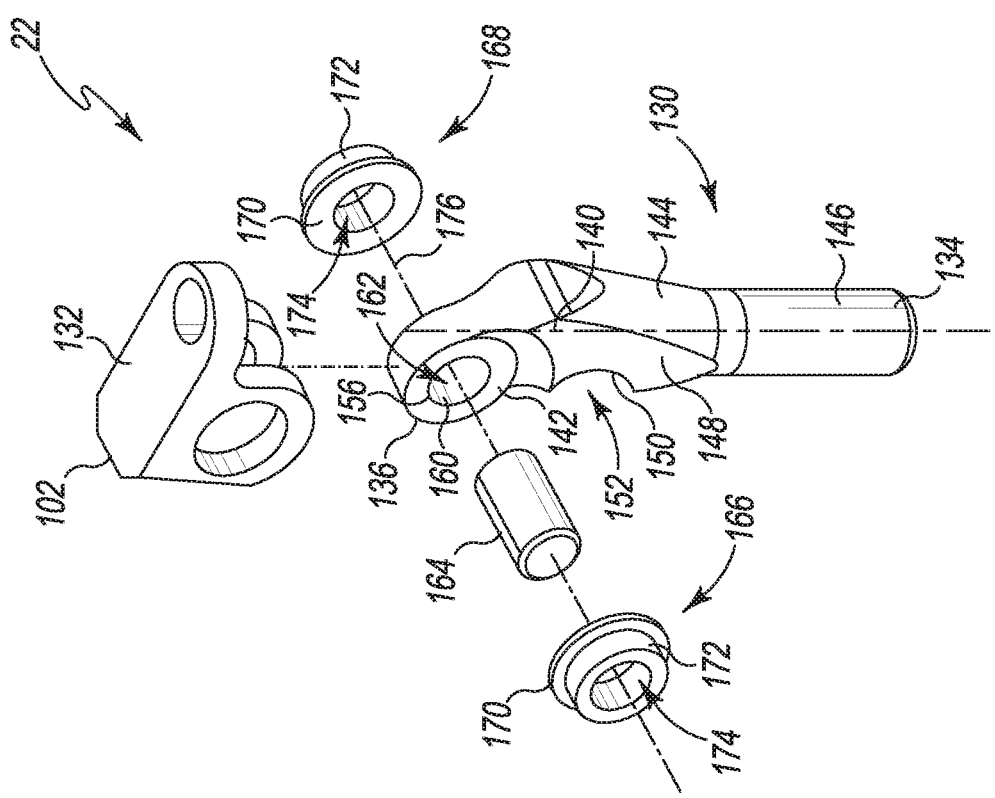
FIG. 5 is an exploded perspective view of a modular insert of the orthopaedic knee prosthesis system of FIG. 1.

Referring now to FIGS. 5-6, the modular insert 22 includes an elongated stem 130 that is pivotally coupled to a bracket 132 sized to be positioned in the intercondylar notch 34 of the femoral component 12. The elongated stem 130 extends from a distal end 134 sized to be positioned in the aperture 68 of the tibial insert 20 to a proximal end 136 configured to be coupled to the bracket 132. The elongated stem 130 has a longitudinal axis 140 that is positioned to be coincident with the longitudinal axis 58 of the tibial insert 20 when the stem is positioned in the aperture 68.

In the illustrative embodiment, the elongated stem 130 has a spine 142 that extends distally from the proximal end 136 and is connected to a trunk 144 that extends proximally from the distal end 134. The trunk 144 has a cylindrical distal section 146 and a faceted proximal section 148. The proximal section 148 includes a concave curved posterior surface 150 that defines a notch 152 sized and shaped to receive the curved anterior surface 94 of the femoral component 12.

The spine 142 of the elongated stem 130 has a medial opening (not shown), a lateral opening 156 that is positioned opposite the medial opening, and an inner wall 160 extending between the openings 156, 158. The inner wall 160 defines a cylindrical passageway 162 extending through the spine 142 that is sized to receive a hinge pin 164, as described in greater detail below.

The modular insert 22 also includes bushings 166, 168, which are sized and shaped to be positioned at either end of the passageway 162 of the spine 142. Each of the bushings 166, 168 includes an inner flange 170 configured to engage the sides of the spine 142 and a sleeve 172 extending outwardly from the flange 170. A passageway 174 extends through each bushing 166, 168, which is sized to receive an end of the hinge pin 164. The passageways 162, 174 and the hinge pin 164 cooperate to define a rotational axis 176 about which the femoral component 12 articulates when assembled with the modular insert 22.

As described above, the modular insert 22 includes a bracket 132 sized to be positioned in the intercondylar notch 34 of the femoral component 12. As shown in FIG. 6, the bracket 132 include a base plate 180 and a pair of arms 182, 184 that extends inferiorly from the base plate 180. The arms 182, 184 are spaced apart such that a channel 186 sized to receive the spine 142 of the elongated stem 130 is defined between the arms. Each of the arms 182, 184 also has a bore 188 that opens into the channel 186. The bores 188 are aligned and are sized to receive the sleeves 172 of the bushings 166, 168.

As described above, the modular insert 22 includes a flange 102, which extends posteriorly from the base plate 180, and is sized to be received in the groove 100 of the femoral component 12. The modular insert 22 also includes a bore 190 that extends in an inferior-superior direction through the anterior end of the base plate 180. As described in greater detail in regard to FIGS. 7-8, the bore 190 is sized to receive a fastener 192 that, along with the flange 102, is configured to couple the modular insert 22 to the femoral component 12.

As described above, the bracket 132 is sized to be positioned in the intercondylar notch 34 of the femoral component 12. In the illustrative embodiment, the bracket 132 has a medio-lateral width 194 that is defined between the sidewalls of the base plate 180. The medio-lateral width 194 is less than or equal to the width 84 of the intercondylar notch 34 to permit the bracket 132 to be inserted into the notch. In the illustrative embodiment, hinge pin 164 extends a length that is equal to the medio-lateral width 194 so that it can also be inserted into the notch 34.

In the illustrative embodiment, the elongated stem 130, the bracket 132, and the hinge pin 164 are formed from an implant-grade metallic material such as, for example, cobalt chromium. The bushings 166, 168 are formed from an implant-grade plastic material such as, for example, ultra-high molecular weight polyethylene (UHMWPE). It should be appreciated that in other embodiments portions of, for example, the stem 130 or the bracket 132 may be formed from implant-grade plastic materials.

Figure 7:
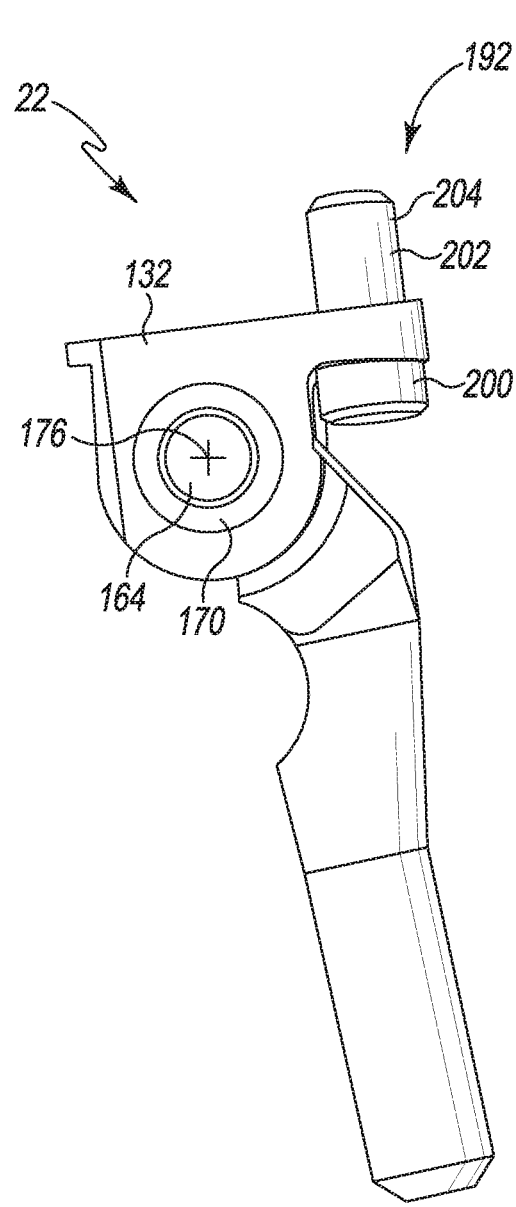
FIG. 7 is a side perspective view of the modular insert of FIGS. 5-6 and a fastener of the orthopaedic knee prosthesis system of FIG. 1.
Figure 8:
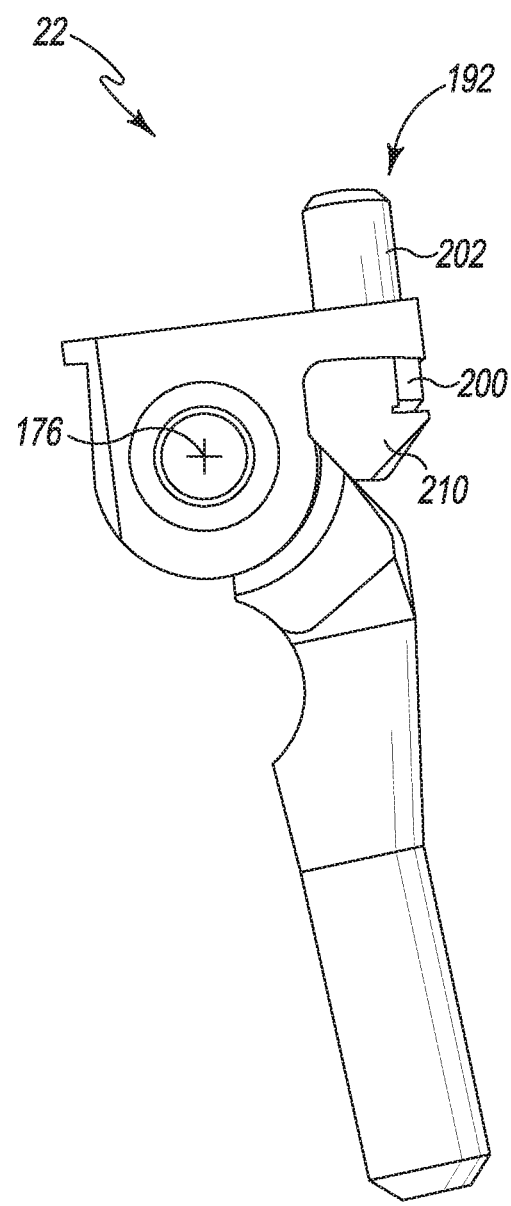
FIG. 8 is a view similar to FIG. 7 illustrating a plug of the orthopaedic knee prosthesis system of FIG. 1.

As shown in FIGS. 7-8, the fastener 192 includes a head 200 and an elongated shaft 202 that extends away from the head 200. The bracket 132 is also formed from an implant-grade metallic material such as, for example, cobalt chromium. The shaft 202 is illustratively cylindrical and includes a substantially smooth outer surface 204. The shaft 202 extends outwardly from the bore 190 defined in the bracket 132 and is sized to engage the smooth distal wall section 118 of the femoral component 12. In the illustrative embodiment, the fastener 192 couples the bracket 132 (and hence the modular insert 22) to the femoral component 12 via a press-fit between the wall section 118 and the shaft 202. It should be appreciated that in other embodiments the section 118 and the shaft 202 may include corresponding threads to couple the component 12 to the insert 22.

Figure 9:
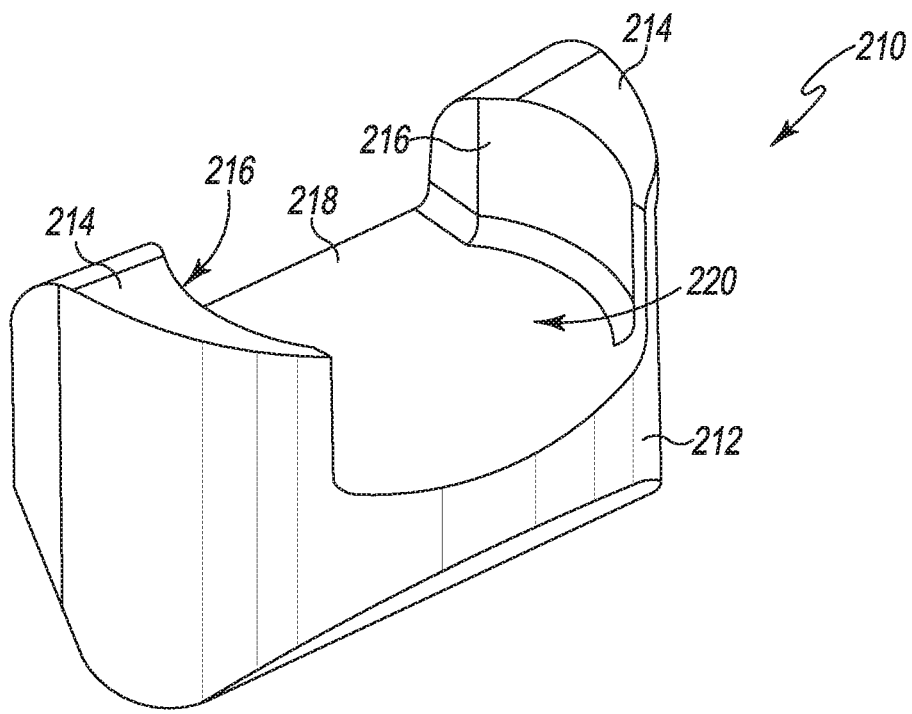
FIG. 9 is a perspective view of the plug of FIG. 8.

The modular insert 22 also includes a plug 210 configured to be coupled to the head 200 of the fastener 192. The plug 210 is illustrative formed from an elastomeric material such as, for example, rubber. The plug 210 includes a main body 212 and a pair of arms 214 that extend outwardly from the main body 212. As shown in FIG. 9, each arm 214 includes a curved inner surface 216 that is shaped to engage the head 200 of the fastener 192. The inner surfaces 216 cooperate with a superior surface 218 of the main body 212 to form a slot 220 sized to receive and retain the head 200 of the fastener 192.

Figure 10:
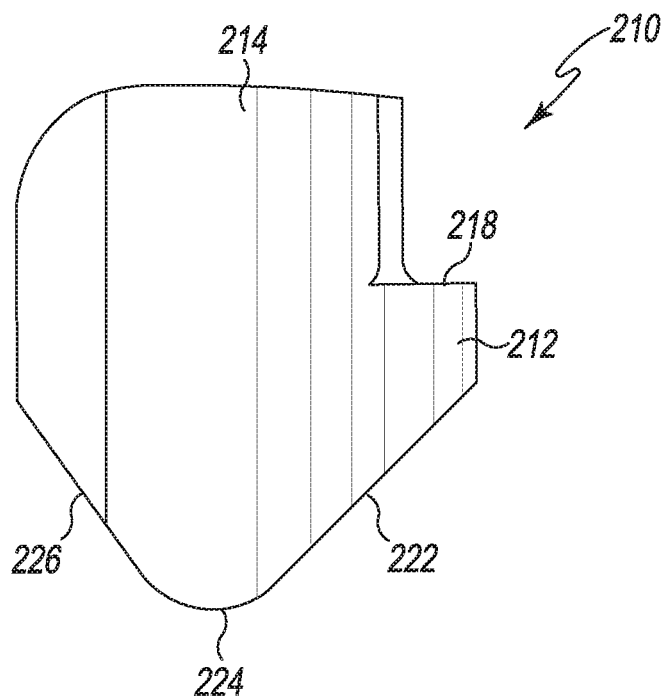
FIG. 10 is a side elevation view of the plug of FIGS. 9-10.
Figure 11:
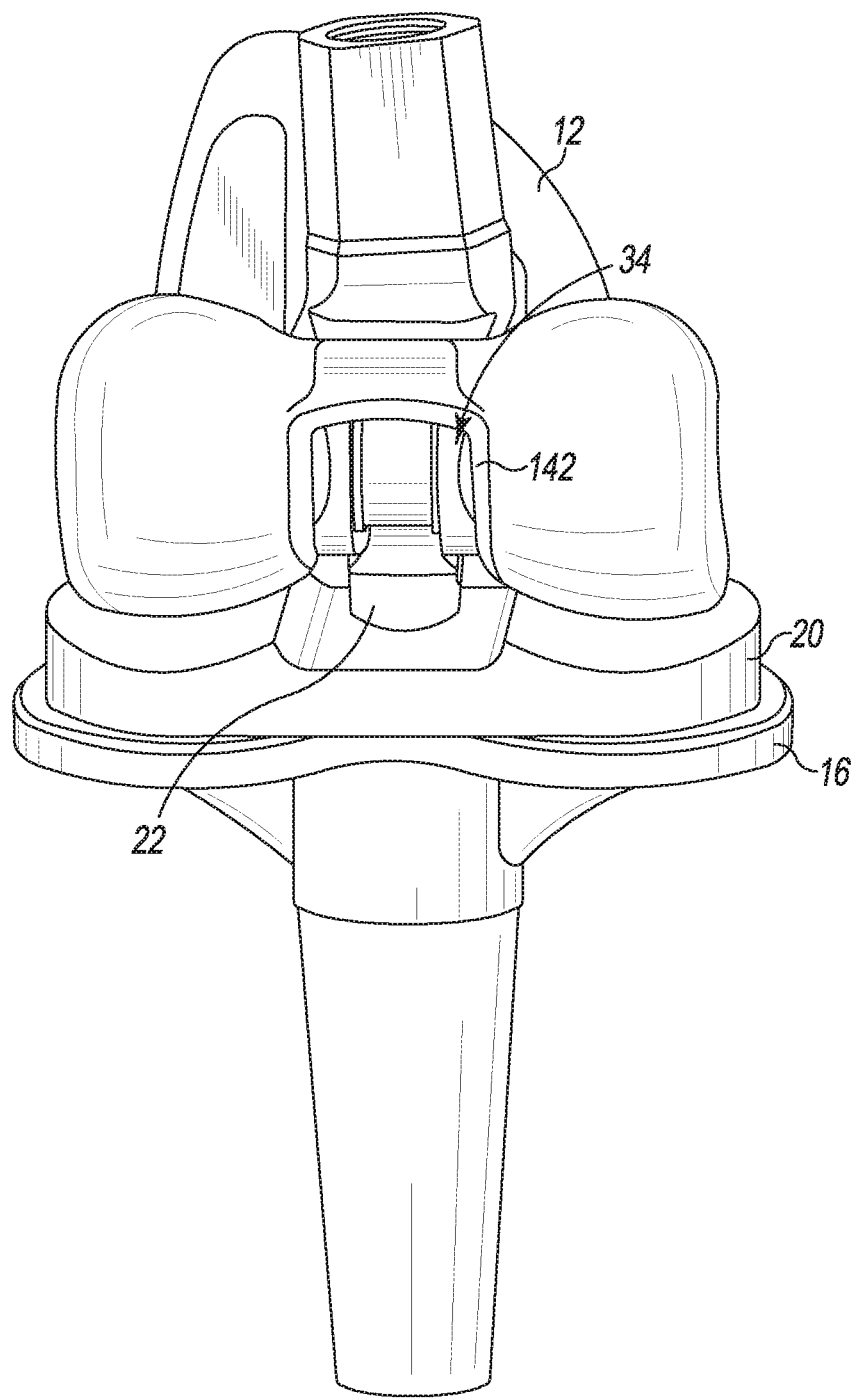
FIG. 11 is a rear perspective view of an assembled orthopaedic knee prosthesis of the system of FIG. 1.
Figure 13:
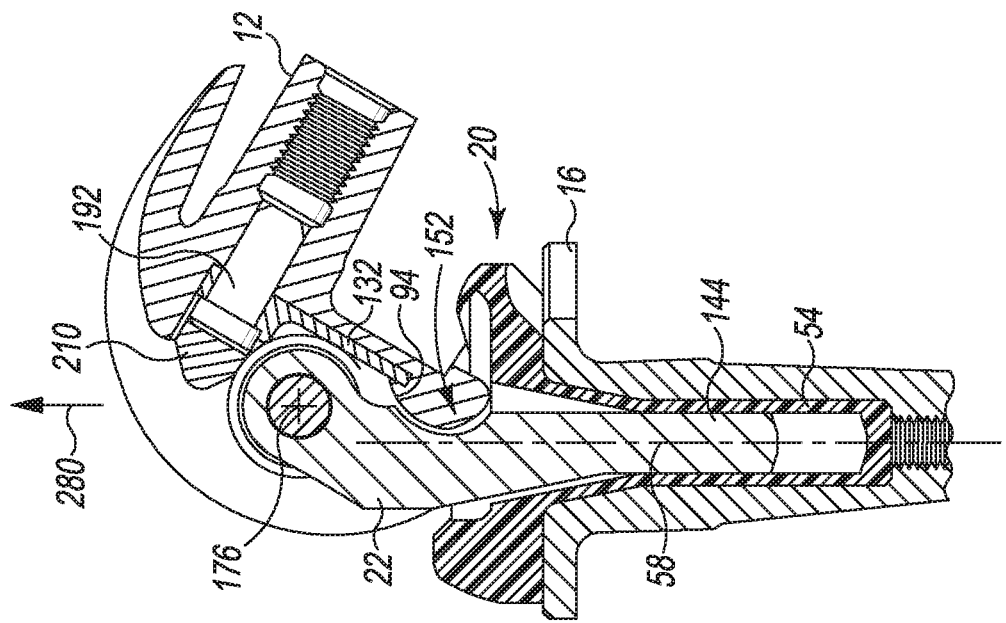
FIG. 13 is a view similar to FIG. 12 showing the assembled orthopaedic knee prosthesis in flexion.

As shown in FIG. 10, the main body 212 is wedge-shaped and includes an anterior surface 222 that extends from the superior surface 218 to an inferior tip 224. A posterior surface 226 extending at an oblique angle relative to the anterior surface 222 extends from the superior surface 218 to the inferior tip 224. As described in greater detail below, the posterior surface 226 is shaped to engage the anterior surface of the spine 142 of the modular insert 22 when the femoral component 12 is in extension.

Returning to FIG. 1, the femoral component 12 and the tibial tray 16 may also be combined with the tibial insert 18 to form another orthopaedic prosthesis, as described above. The tibial insert 18 includes a platform 252 that is sized to be positioned on the proximal surface 42 of the tibial tray 16 and an elongated stem 254 that extends inferiorly from a distal surface 256 of the platform 252 along a longitudinal axis 258. The distal surface 256 of the platform 252 is substantially planar. The platform 252 also includes a pair of concave curved proximal surfaces 260, 262 that correspond to the lateral and medial condyle surfaces 30, 32 of the femoral component 12. The platform 252 also includes a curved outer wall 264 extends between the surfaces 260, 262, 256.

The tibial insert 18 also includes a spine 266 that extend superiorly from the platform 252 between the pair of concave curved proximal surfaces. The spine 266 includes a convex curved anterior surface 268 and a concave curved posterior surface 270. The concave curved posterior surface 270 is shaped to engage the convex curved anterior surface 94 of the posterior cam 90 of the femoral component 12.

When coupled to the tibial tray 16, the distal surface 256 of the tibial insert 18 engages the proximal surface 42 of the tibial tray. The elongated stem 254 of the tibial insert 18 is sized to be received in the aperture 48 of the tibial tray 16 when the tibial insert 18 is coupled to the tibial tray 16. In the illustrative embodiment, the stem is sized and shaped to permit the tibial insert 18 to rotate about the longitudinal axis 258 when positioned in the aperture 48 of the tibial tray 16.

In use, a patient may initially have implanted, for example, a rotating platform orthopaedic prosthesis with the femoral component 12, the tibial tray 16, and tibial insert 18. Due to injury, bone loss, or other degradation of the patient's mobility, a surgeon may determine that the existing orthopaedic prosthesis may need to be replaced with a hinged orthopaedic prosthesis. To do so, the surgeon may open the patient's soft tissue in the region surrounding the knee joint. The surgeon may then remove some or all of the components of the existing orthopaedic prosthesis, surgically-prepare the patient's bones to receive a new femoral component 12, tibial tray 16, tibial insert 20, and modular insert 22, and then implant those components in the patient's joint.

In some surgeries, the surgeon may choose to remove the tibial insert 18 and leave one or both of the existing femoral component 12 and the tibial tray 16 implanted in the patient's joint. The surgeon may perform a trial reduction to select a modular insert 22 and tibial insert 20 of appropriate size. To attach the tibial insert 20 to the tibial tray 16, the surgeon may align the elongated stem 54 of the insert 20 with the aperture 48 of the tibial tray 16 and advance the distal tip of the stem 54 into the aperture 48 to engage the platform 52 with the base 36 of the tray 16. To couple the modular insert 22 to the tibial insert 20, the surgeon may align the trunk 144 of the modular insert 22 with the aperture 68 of the tibial insert 20 and advance the distal tip of the trunk 144 into the aperture 68 to seat the modular insert 22 on the tibial insert 20.

Figure 12:
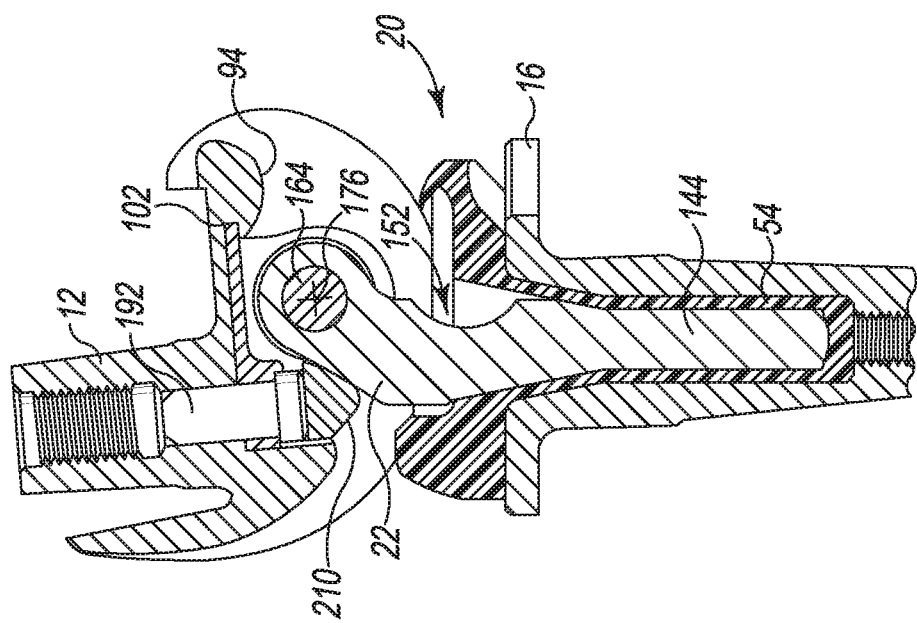
FIG. 12 is a cross-sectional side elevation view of the assembled orthopaedic knee prosthesis taken along the line 12-12 in FIG. 11.

To couple the modular insert 22 to the femoral component 12, the surgeon may advance the retaining flange 102 of the bracket 132 of the modular insert 22 into the groove 100 defined in the posterior cam 90 of the femoral component 12, as shown in FIG. 12. The surgeon may also align the bore 190 with the passageway 116 of the femoral component 12 and advance the elongated shaft 202 of the fastener 192 through the bore 190 and into the passageway 116. When the head 200 of the fastener 192 engages the bracket 132, the bracket 132 (and hence the modular insert 22) is coupled to the femoral component 12 via a press-fit between the wall section 118 defining the passageway 116 and the shaft 202. The surgeon may attach the plug 210 to the head 200 of the fastener 192 to form the hinged orthopaedic prosthesis shown in FIG. 12.

When the orthopaedic prosthesis is in extension as shown in FIG. 12, the plug 210 engages the anterior surface of the spine 142 of the modular insert 22, and the femoral condyles 28 engages the proximal surfaces 60, 62 of the tibial insert 20. When the knee joint is moved from extension to flexion, the femoral component 12 is pivoted above the axis 176 extending through the hinge pin 164. As the femoral component 12 pivots, the surface geometry of the femoral condyles causes the modular insert 22 to advance superiorly in the direction indicated by arrow 280 in FIG. 12 while the tibial insert 20 remains engaged with the tibial tray 16. At full flexion, the posterior cam 90 is positioned in the notch 152 defined in the modular insert 22 with its anterior surface 94 engaged with the posterior surface 150 of the modular insert 22, thereby preventing further flexion. It should be appreciated that the femoral component 12, tibial insert 20, and modular insert 22 are configured to pivot about the axis 58, which extends orthogonal to the hinge pin axis 176, during normal movement and use of the orthopaedic prosthesis.

Figure 14:
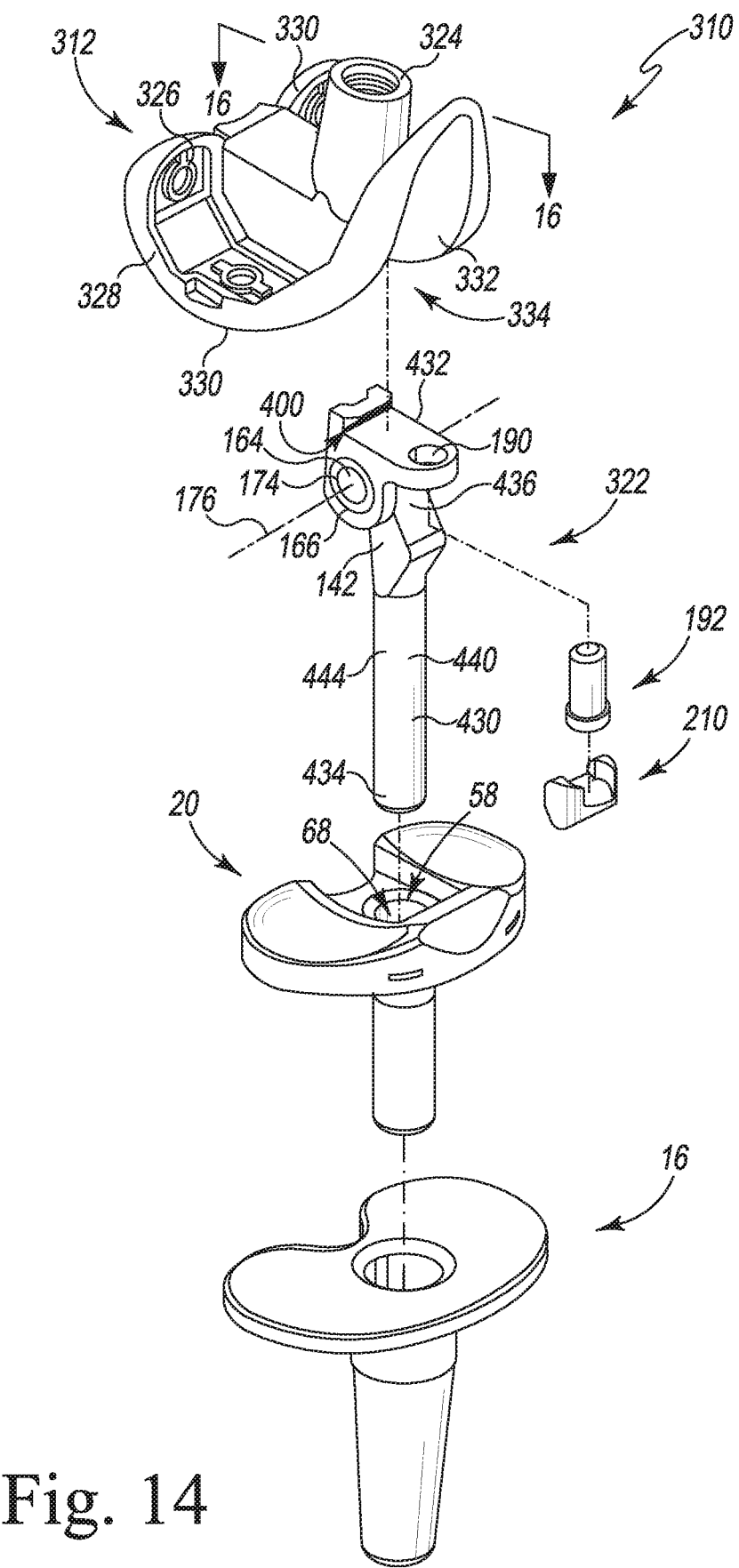
FIG. 14 is an exploded perspective view of another embodiment of an orthopaedic knee prosthesis system.

Referring now to FIGS. 14-17, another embodiment of a hinged orthopaedic prosthesis (hereinafter prosthesis 310) is shown. The orthopaedic knee prosthesis 310 includes a femoral component 312 configured to be coupled to a distal end of a patient's femur, a tibial tray 16 that is configured to be coupled to a proximal end of a patient's femur, and a tibial insert 20 configured to be assembled with the tibial tray 16. It should be appreciated that the tibial insert and tibial tray of the prosthesis 310 are identical to the tibial insert and tibial tray described above in regard to FIGS. 1-13, and the same references numbers will be used to identify features of those components. Additionally, some of the features of the other components of the prosthesis 310 are the same or similar to the features described above in regard to FIGS. 1-13, and the same references numbers will be used to identify those features. As shown in FIG. 14, the prosthesis 310 also includes a modular insert 322 configured to couple the tibial insert 20 to the femoral component 312.

Similar to the femoral component 12, the femoral component 312 is formed from an implant grade metallic material such as, for example, cobalt chromium. As shown in FIGS. 14-17, the femoral component 312 includes a post 324 that is configured to be implanted into the distal end of the patient's femur. The post 324 is attached to a body 326 having a pair of spaced-apart lateral and medial condyles 328. The condyles 328 include respective lateral and medial condyle surfaces 330, 332, which are curved convexly. An intercondylar notch 334 is defined between the lateral and medial condyles 328 and is sized to receive the modular insert 322.

Each condyle 328 includes a sidewall 380 that extends distally from a respective condyle surface 330, 332 to a base wall 382. The intercondylar notch 334 has a width that is defined between the sidewalls 380, which is sized to receive the proximal end of the modular insert 322, as described in greater detail below. The base wall 382 includes a posterior edge 384 that is sized to be received in a retaining groove 400 defined in the modular insert 322, also as described in greater detail below.

An opening 110 is defined in the base wall 382, and an inner wall 112 extends proximally from the opening 110 through the post 324 to an opening 114 defined in the proximal end of the post. The inner wall 112 and the openings 110, 114 define a passageway 116 extending through the post 324. The inner wall 112 includes a substantially smooth distal section 118 that is connected to a threaded proximal section 120.

Returning to FIG. 14, the modular insert 322 includes an elongated stem 430 that is pivotally coupled to a bracket 432 sized to be positioned in the intercondylar notch 334 of the femoral component 312. The elongated stem 430 extends from a distal end 434 sized to be positioned in the aperture 68 of the tibial insert 20 to a proximal end 436 configured to be coupled to the bracket 432. The elongated stem 430 has a longitudinal axis 440 that is positioned to be coincident with the longitudinal axis 58 of the tibial insert 20 when the stem is positioned in the aperture 68.

In the illustrative embodiment, the elongated stem 430 has a spine 142 that extends distally from the proximal end 436 and is connected to a trunk 444 that extends proximally from the distal end 434. The trunk 444 has a cylindrical body, as shown in FIG. 14. The spine 142 of the elongated stem 430 has a cylindrical passageway 162 (see FIG. 17) that is sized to receive a hinge pin 164. The modular insert 322 also includes a pair of bushings 166, 168, which are sized and shaped to be positioned at either end of the passageway 162 of the spine 142. A passageway 174 extends through each bushing 166, 168, which is sized to receive an end of the hinge pin 164. The passageways 162, 174 and the hinge pin 164 cooperate to define a rotational axis 176 about which the femoral component 312 articulates when assembled with the modular insert 322.

Figure 15:
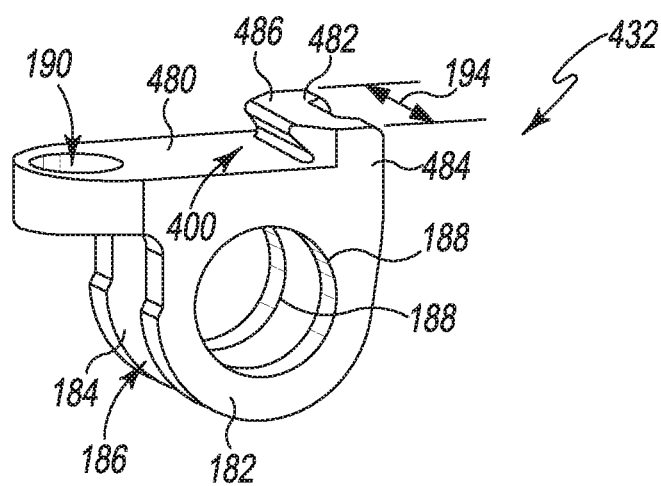
FIG. 15 is a perspective view of a bracket of the orthopaedic knee prosthesis system of FIG. 14.
Figure 16:
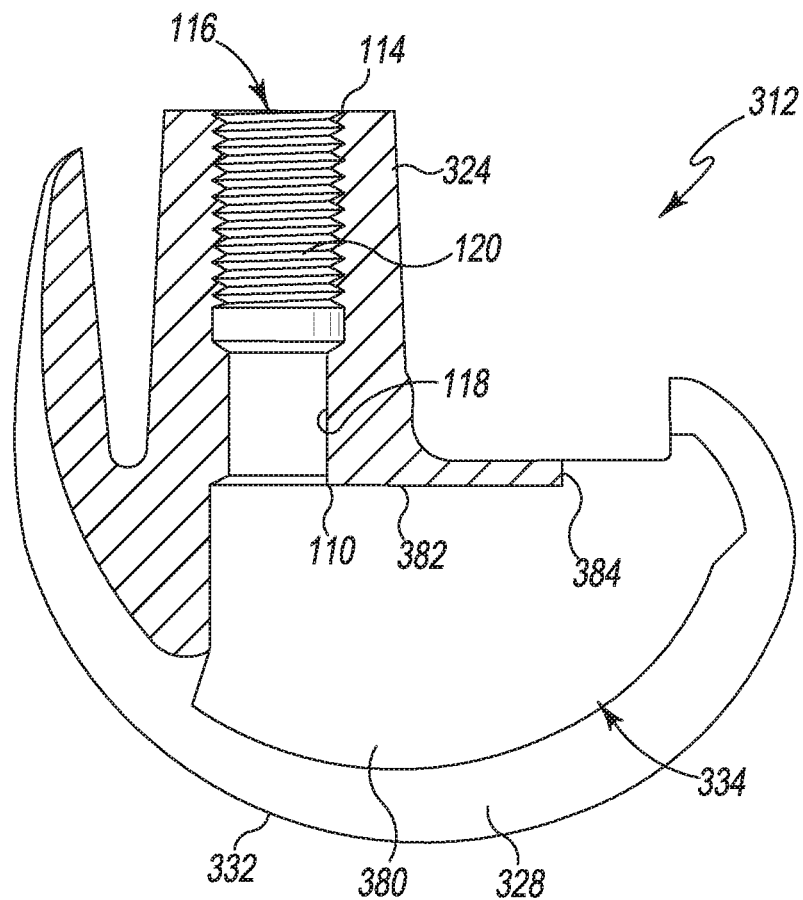
FIG. 16 is a cross-sectional side elevation view of a femoral component of the orthopaedic knee prosthesis system taken along the line 16-16 in FIG. 14.

As described above, the modular insert 322 includes a bracket 432 sized to be positioned in the intercondylar notch 334 of the femoral component 312. As shown in FIG. 15, the bracket 432 include a base plate 480 and a pair of arms 182, 184 that extends inferiorly from the base plate 480. The arms 182, 184 are spaced apart such that a channel 186 sized to receive the spine 142 of the elongated stem 430 is defined between the arms. Each of the arms 182, 184 also has a bore 188 that opens into the channel 186. The bores 188 are aligned and are sized to receive the sleeves 172 of the bushings 166, 168.

As described above, the modular insert 322 includes a retaining groove 400, which is defined between the posterior end of the base plate 480 and a retaining flange 482 extending outwardly from the base plate 480. As shown in FIG. 15, the flange 482 includes an arm 484 extending superiorly from the base plate 480, and another arm 486 extending anteriorly from the end of the arm 484. The arm 486 is spaced apart from the base plate 480 such that the groove 400 is defined between the arms 484, 486 and the base plate 480.

The modular insert 322 also includes a bore 190 that extends in an inferior-superior direction through the anterior end of the base plate 480. As described above in regard to FIGS. 1-13, the bore 190 is sized to receive a fastener 192 (see FIGS. 14-15) that, along with the flange 482, is configured to couple the modular insert 322 to the femoral component 312.

As described above, the bracket 432 is sized to be positioned in the intercondylar notch 334 of the femoral component 312. In the illustrative embodiment, the bracket 432 has a medio-lateral width 194 that is defined between the sidewalls of the base plate 480. The medio-lateral width 194 is less than or equal to the width of the intercondylar notch 334 to permit the bracket 432 to be inserted into the notch. In the illustrative embodiment, hinge pin 164 extends a length that is equal to the medio-lateral width 194 so that it can also be inserted into the notch 334.

Figure 17:
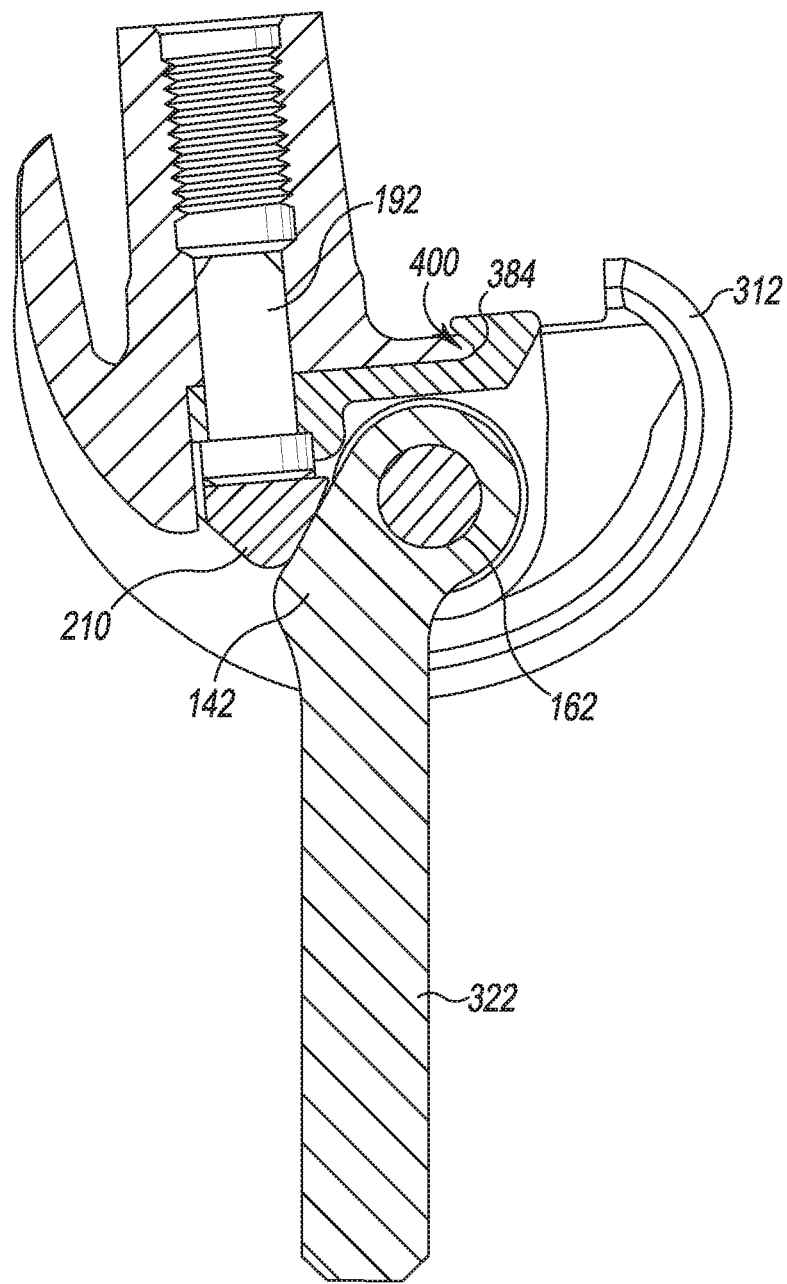
FIG. 17 is a cross-sectional side elevation view of a portion of the orthopaedic knee prosthesis system of FIG. 14.

Referring now to FIG. 17, the surgeon may advance the retaining edge 384 of the femoral component 312 into the groove 400 of the bracket 432 to couple the modular insert 322 to the femoral component 312. The surgeon may also align the bore 190 with the passageway 116 of the femoral component 312 and advance the elongated shaft 202 of the fastener 192 through the bore 190 and into the passageway 116. When the head 200 of the fastener 192 engages the bracket 432, the bracket 432 (and hence the modular insert 322) is coupled to the femoral component 312 via a press-fit between the wall section 118 defining the passageway 116 and the shaft 202. The surgeon may attach the plug 210 to the head 200 of the fastener 192 to form the hinged orthopaedic prosthesis shown in FIG. 17. When the orthopaedic prosthesis is in extension as shown in FIG. 17, the plug 210 engages the anterior surface of the spine 142 of the modular insert 22, and the femoral condyles 328 engage the proximal surfaces 60, 62 of the tibial insert 20 (not shown in FIG. 17).

Figure 18:
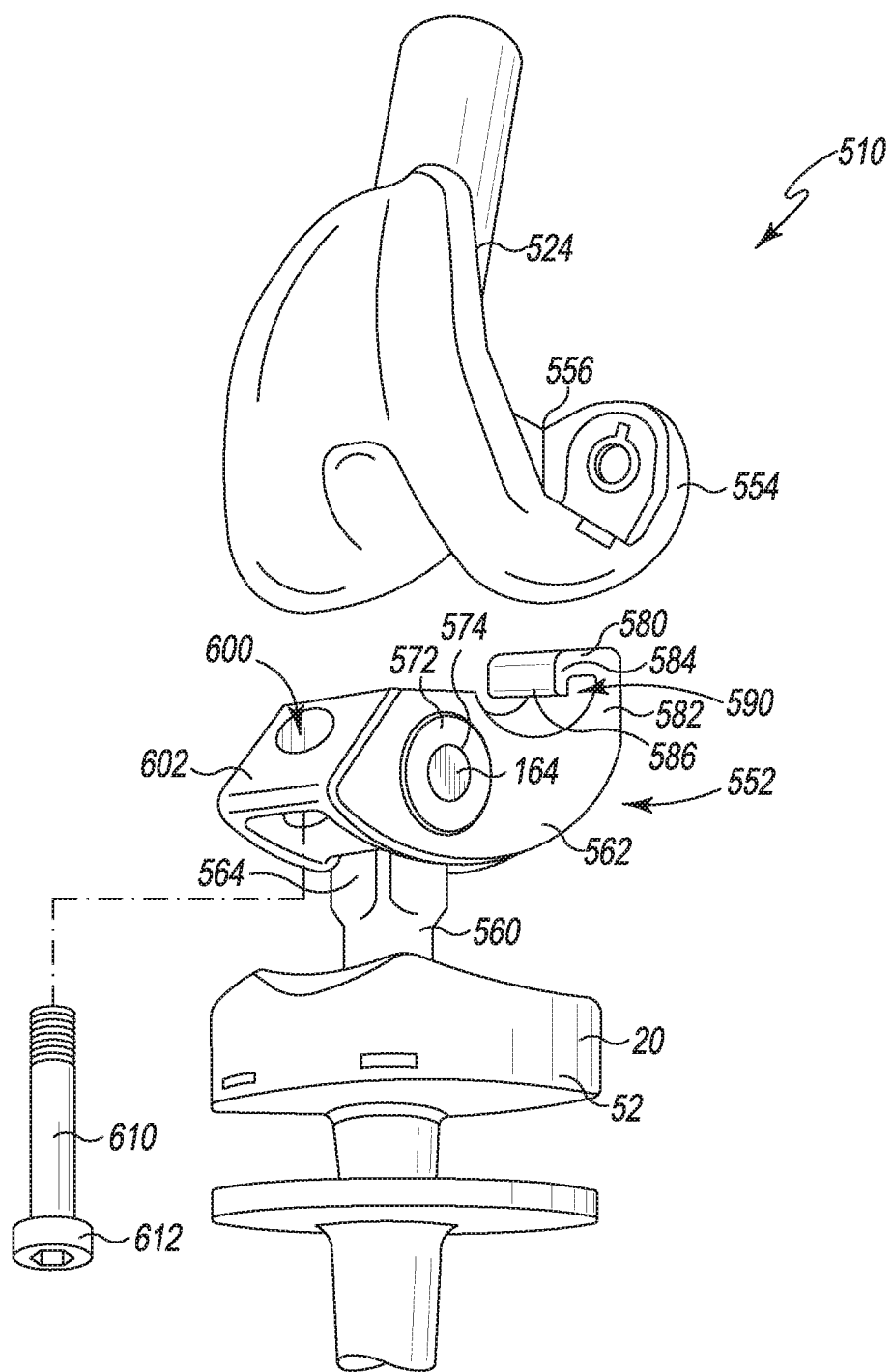
FIG. 18 is an exploded view of another embodiment of an orthopaedic knee prosthesis system.

Referring now to FIG. 18, another embodiment of an orthopaedic knee prosthesis 510 includes several similar components to the orthopaedic knee prosthesis system 10, which are referenced with the same reference numbers. The prosthesis 510 includes a modular insert 552 that is configured to be coupled the tibial insert 20 to a femoral component 554. In some embodiments, the femoral component 554 may be the same as the femoral component 12. In other embodiments, the femoral component 554 does not include a groove formed in an anterior surface of the posterior cam 556.

The modular insert 552 includes an elongated stem 560 coupled to a bracket 562. The elongated stem 560 is configured to be inserted into the aperture 68 of the platform 52 of the tibial insert 20 and extend in an inferior-superior direction. The bracket 562 is hingedly attached to a spine 564 of the elongated stem 560. The bracket 562 includes bores (not shown) extending in a medial-lateral direction and configured to receive a hinge pin 164. The hinge pin 164 extends through an opening (not shown) in the spine 564 of the elongated stem 560. In the illustrative embodiment, a pair of bushings 572 is positioned in the bores 566 so that the hinge pin 164 extends through openings 574 in the bushings 572. The bracket 562 pivots about the hinge pin 164 relative to the elongated stem 560.

The bracket 562 includes a flange 580 extending from a posterior end 582 of the bracket 562. The flange 580 includes a posterior arm 584 extending from the posterior end 582 of the bracket 562. An arm 586 extends inferiorly from the posterior arm 584. The arms 584, 586 form a notch 590. The flange 580 is configured to couple to the posterior cam 556 of the femoral component 554 to at least partially secure the bracket 562 to the femoral component 554.

A bore 600 extends through an anterior end 602 of the bracket 562. The bore 600 is configured to receive a fastener 610 that is extended into the passageway 116 in the post 524 of the femoral component 554. The fastener 610 extends transverse to the hinge pin 164. In some embodiments, the fastener 610 is a threaded screw that is threaded into the bore 600 extending through the post 524. In some embodiments, the fastener 610 is a captured screw that is captured in the bracket 662 and allowed to rotate so that the captured screw can be threaded into the passageway 116 extending through the post 524. In some embodiments, a plug, as described above, may be positioned on an end 612 of the fastener 610. The plug may be provided to limit extension of the prosthesis 510.

The exemplary embodiments of the present disclosure are described and illustrated below to encompass prosthetic knee joints and knee joint components, as well as methods of implanting and reconstructing knee joints. It will also be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

The invention claimed is:

1. An orthopaedic prosthesis, comprising:
   a femoral component configured to be coupled to a surgically-prepared distal end of a patient's femur, the femoral component including (i) a pair of condyles spaced apart to define an intercondylar notch, each condyle including a convex curved condylar surface, and (ii) a posterior cam that is positioned in the intercondylar notch, the posterior cam having a groove formed in an anterior surface thereof,
   a tibial component including a tray configured to be coupled to a surgically-prepared proximal end of a patient's tibia and a platform pivotally coupled to the tray, the platform including a pair of concave curved surfaces corresponding to the convex curved condylar surfaces of the femoral component and a proximal opening positioned between the concave curved surfaces, and
   a modular insert configured to be selectively coupled to the femoral component, the modular insert including (i) a bracket sized to be positioned in the intercondylar notch of the femoral component, the bracket having a flange extending posteriorly therefrom and positioned in the groove formed in the anterior surface of the posterior cam of the femoral component, (ii) an elongated stem sized to be received in the opening defined in the platform of the tibial component, the elongated stem including a posterior surface configured to engage the anterior surface of the posterior cam of the femoral component, and (iii) a hinge pin that pivotally couples the elongated stem to the bracket,
   wherein (i) the platform rotates relative to the tray about a first axis extending in an inferior-superior direction, and (ii) the bracket and the femoral component pivot about a second axis relative to the elongated stem, the second axis extending in a medial-lateral direction orthogonal to the first axis.

2. The orthopaedic prosthesis of claim 1, wherein:
   the bracket of the modular insert includes a bore that is offset from the elongated stem, and
   the fastener is configured to extend through the bore to couple the modular insert to the femoral component.

3. The orthopaedic prosthesis of claim 2, wherein:
   the femoral component includes a post that is positioned opposite the pair of condyles and a passageway extending into the post, and
   the fastener is configured to extend into the passageway.

4. The orthopaedic prosthesis of claim 2, wherein the bracket includes an inferior surface and a superior surface, and the bore extends from an opening in the inferior surface to an opening in the superior surface.

5. The orthopaedic prosthesis of claim 1, wherein the fastener extends along an axis that is angled relative to an inferior/superior axis of the elongated stem.

6. The orthopaedic prosthesis of claim 1, wherein the hinge pin is sized to be positioned in the intercondylar notch of the femoral component between the pair of condyles.

7. The orthopaedic prosthesis of claim 1, wherein:
   the femoral component further includes a base surface and a pair of planar inner side walls extending from the base surface,
   the base surface and the inner side walls partially define the intercondylar notch, and
   the hinge pin is sized to be positioned between the inner side walls of the femoral component.

8. The orthopaedic prosthesis of claim 7, wherein the bracket includes a pair of outer side walls that are spaced a distance less than a distance between the inner side walls of the femoral component.

* * * * *